United States Patent [19]
Chemelli et al.

[11] Patent Number: 5,593,804
[45] Date of Patent: Jan. 14, 1997

[54] TEST POUCH

[75] Inventors: John B. Chemelli, Webster; Walter J. Bernecker; Craig A. Caprio, both of Rochester, all of N.Y.

[73] Assignee: Eastman Kodak Company, Rochester, N.Y.

[21] Appl. No.: 567,751

[22] Filed: Dec. 5, 1995

[51] Int. Cl.$^6$ .................................................. G03C 5/02
[52] U.S. Cl. .................................... 430/30; 430/401
[58] Field of Search ...................................... 430/30, 401

[56] References Cited

U.S. PATENT DOCUMENTS

| | | | |
|---|---|---|---|
| 3,036,894 | 5/1962 | Forestiere | 436/165 |
| 3,476,515 | 11/1969 | Johnson et al. | 436/165 |
| 3,697,227 | 10/1972 | Goldstein et al. | 422/61 |
| 3,700,335 | 10/1972 | Seelbinder | 430/30 |
| 3,713,779 | 1/1973 | Sirago et al. | 422/61 |
| 3,725,071 | 4/1973 | Seelbinder et al. | 430/30 |
| 3,799,742 | 3/1974 | Coleman | 422/61 |
| 3,864,082 | 2/1975 | Kato | 436/34 |
| 4,065,263 | 12/1977 | Woodbridge | 23/253 TP |
| 4,859,421 | 8/1989 | Apicella | 422/21 |
| 5,116,576 | 5/1992 | Stanley | 422/55 |
| 5,212,098 | 5/1993 | Hoffmann et al. | 436/125 |
| 5,229,297 | 7/1993 | Schnipelsky et al. | 436/94 |
| 5,254,479 | 10/1993 | Chemelli | 436/180 |
| 5,288,463 | 2/1994 | Chemelli | 422/58 |
| 5,290,518 | 3/1994 | Johnson | 422/58 |

*Primary Examiner*—Hoa Van Le
*Attorney, Agent, or Firm*—Susan L. Parulski

[57] ABSTRACT

Method and an apparatus for measuring the development parameter of a light-sensitive fluid in a white-light environment. The apparatus comprises first and second flexible light-impervious sheets superimposed and sealed together to form a pouch containing a plurality of chambers having flow paths therebetween, wherein the chambers are sealed with burstable seals allowing fluid communication between the chambers upon the application of a predetermined pressure.

3 Claims, 2 Drawing Sheets

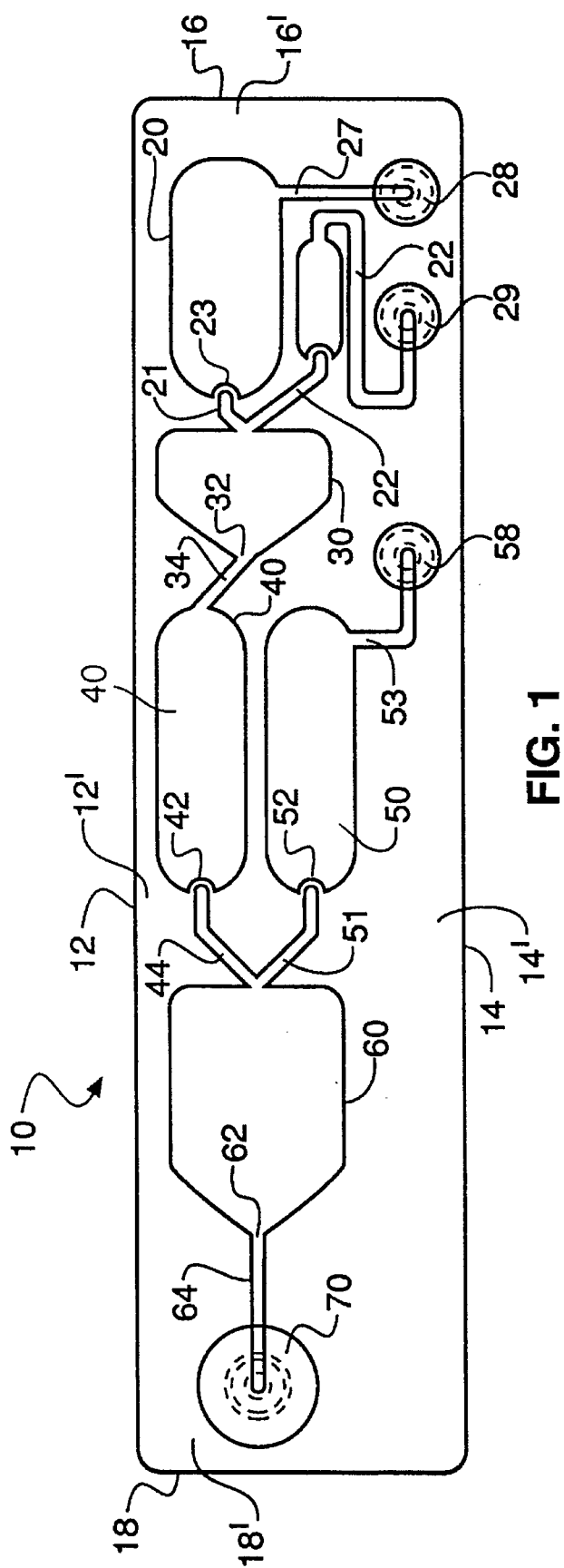
FIG. 1
FIG. 2

TEST POUCH

FIELD OF THE INVENTION

The present invention relates to a method and an apparatus for measuring the development of a liquid photographic emulsion. More particularly, the present invention relates to a method, and an apparatus used with the method for measuring silver particles in a photographic emulsion by the use of an infrared light source before the emulsion is coated on a substrate.

BACKGROUND OF THE INVENTION

The prior art has addressed the need to measure photographic properties of silver halide emulsions in order to provide and to consistently maintain the desired photographic properties in such emulsions. One of the methods used for such measurement is a sensitrometric method in which a part of the photographic emulsion is coated on a support or carrier, dried, exposed for development, fixed, and the blackened density of the layer is measured sensitometrically. If the so-produced layer does not have the desired photographic properties, the emulsion is generally referred to as being "fogged". This method is time consuming and its success is largely dependent on the skill of the operator performing the testing. In addition, much time, effort and materials are wasted if the emulsion is fogged.

Another method, disclosed by U.S. Pat. No. 5,212,098, involves titrating of bromide ions present in a non-chromogenic developer containing thiocyanate ions with an aqueous silver nitrate. The method is relatively cumbersome and time consuming.

Still another approach for measuring the progress of the development of liquid photographic emulsions is exemplified by U.S. Pat. No. 3,864,082. This approach comprises a method in which the liquid photographic emulsion is mixed with a developer in a tank, and the emulsion is caused to react with the developer to form reduced silver. Without adding a fixing solution or a stopping solution, the mixture is introduced into a flow cell, and passed through the flow cell for the period of time necessary for measurement. In the flow cell, the mixture is irradiated by light to quantitatively measure the amount of reduced silver using optical means.

While this approach monitors the emulsion, the mixing operation, measurement and the washing/cleaning of the tank and flow cell can influence the outcome of the measurements. Accordingly, it is desirable to test a photographic batch of an emulsion after formulation. It is further desirable to test the emulsion before coating the emulsion onto a support web or paper, since if the emulsion is fogged, materials, effort, and time would be wasted. Such waste could be prevented by testing the emulsion before coating onto the support web or paper.

It is also highly desirable to test photographic emulsions in white-light conditions for ease of operation.

The present invention addresses the needs not quite satisfactorily met by the prior art by providing a consistent, reliable apparatus, and method of use thereof, for measuring photographic properties of an emulsion after formulation and prior to coating the emulsion onto a support, and in white-light conditions.

SUMMARY OF THE INVENTION

The method of measuring the development of a photographic emulsion is accomplished by the use of a pouch-like containment apparatus made of a flexible, polymeric material compatible with photographic reagents, and being a light-impervious material to insure light tightness in white-light conditions. The containment apparatus is relatively flat to allow a mechanical means, such as a o roller, to exert pressure thereon during the method of practicing the invention.

In one aspect the present invention is directed to an apparatus for measuring a development parameter of a light-sensitive fluid in a white-light environment, the apparatus comprising:

first and second flexible sheets superimposed and sealed together to form a pouch having a first chamber, a second chamber, and a mixing chamber, the pouch having a flow path between the chambers, the flexible sheets being made of a light-impervious material;

a light-tight inlet for introducing the light-sensitive fluid to the first chamber;

a developer disposed within the second chamber sufficient to develop the light-sensitive fluid to a light-insensitive mixture;

a first seal positioned across the flow path in between the first chamber and the mixing chamber;

a second seal positioned across the flow path in between the second chamber and the mixing chamber, the first and second seals being burstable by a predetermined pressure applied along the flow path; and a detection site in communication with the mixing chamber and disposed in the white-light environment wherein the development parameter can be measured.

The test pouch is :made of light-impervious material to insure light-tightness so that the measurement may be conveniently accomplished under white-light conditions.

In another aspect the present invention is directed to a method of measuring a development parameter of a light-sensitive fluid in a white-light environment comprising:

introducing a predetermined amount of the light-sensitive fluid into a first chamber of a light-impervious containment apparatus;

heating the light-sensitive fluid to a temperature above 100° C.;

applying a predetermined pressure along a flow path between the first chamber and a mixing chamber of the containment apparatus;

bursting a seal positioned across the flow path between the first chamber and the mixing chamber;

transferring the light-sensitive fluid from the first chamber to the mixing chamber:

mixing the light-sensitive fluid with a sufficient amount of developer in the mixing chamber to develop the light-sensitive fluid to a light-insensitive mixture;

transferring the light-insensitive mixture to a detection site in communication with the mixing chamber and disposed in the white-light environment; and measuring the development parameter in the white-light environment.

In the preferred embodiment the apparatus of the present invention is divided into a succession of at least five chambers connected by conduits or channels, the chambers having burstable sealing means which, by a mechanical pressure means, can be opened to permit transfer of the content of one chamber to a succeeding chamber through the conduits or channels. The apparatus comprises:

a first chamber pre-filled with a measured amount of a developer hermetically sealed therein by a burstable sealing means; the first chamber is connected to a second chamber by a conduit or channel;

a second chamber, having an inlet port, is designed to receive through the inlet port a measured amount of an emulsion just prior to testing the emulsion, the second chamber being connected to a third chamber through a conduit or channel;

a third chamber connected to a fifth chamber by a conduit or channel adapted to receive the content of the second chamber and to serve as a reaction chamber;

a fourth chamber parallel and end-to-end with the third chamber connected to the fifth chamber via a conduit or channel is pre-filled with a measured amount of a fixer through the conduit or channel;

a fifth chamber to simultaneously receive the content of the third chamber and the content of the fourth chamber is adapted to serving as the final reaction chamber; and an exit port located on the fifth chamber through which the reacted mixture content of the fifth chamber can be expelled.

The apparatus further comprises a vial attached to the exit port on the fifth chamber. The vial is adapted to be irradiated by an infrared device so that the silver particles contained in the final reacted mixture can be determined.

In the preferred embodiment of the invention there is provided a method for measuring the development of a photographic emulsion containing silver particles therein by using the above described pouch-like apparatus having first, second, third, fourth and fifth contiguous chambers sealed by burst seals and connected by conduits or channels and a detachable vial attached to the fifth chamber, the method comprising the steps of:

(a) pre-filling the first chamber with a measured amount of a developer;

(b) pre-filling the fourth chamber with a measured amount of a fixer:

(c) adding a measured amount of the emulsion to be tested to the second chamber;

(d) heating the pouch to a temperature ideal for the type of emulsion being heated, preferably to about 100° F., and most preferably to about 103° F.–104° F.;

(e) bursting the developer seal and transferring the developer by external pressure means into the second chamber;

(f) flowing the content of the second chamber into the third chamber by exerting an external pressure onto the second chamber and allowing the mixture a dwell time of about 30 seconds to allow for the reaction of the developer and the emulsion;

(g) exerting an external pressure simultaneously on the third and fourth chambers thereby transferring their contents into the fifth or final reaction chamber and allowing them to mix to obtain a final, reacted emulsion;

(h) transferring the reacted emulsion into a vial attached to the fifth chamber by exerting an external pressure onto the fifth chamber; and (i) taking a photometric reading of the filled vial using an infrared device to determine the amount of silver particles in the reacted emulsion.

BRIEF DESCRIPTION OF THE DRAWINGS

FIG. 1 is a top plan view of the apparatus of the present invention;

FIG. 2 is a longitudinal side view thereof; and

Figure 3:
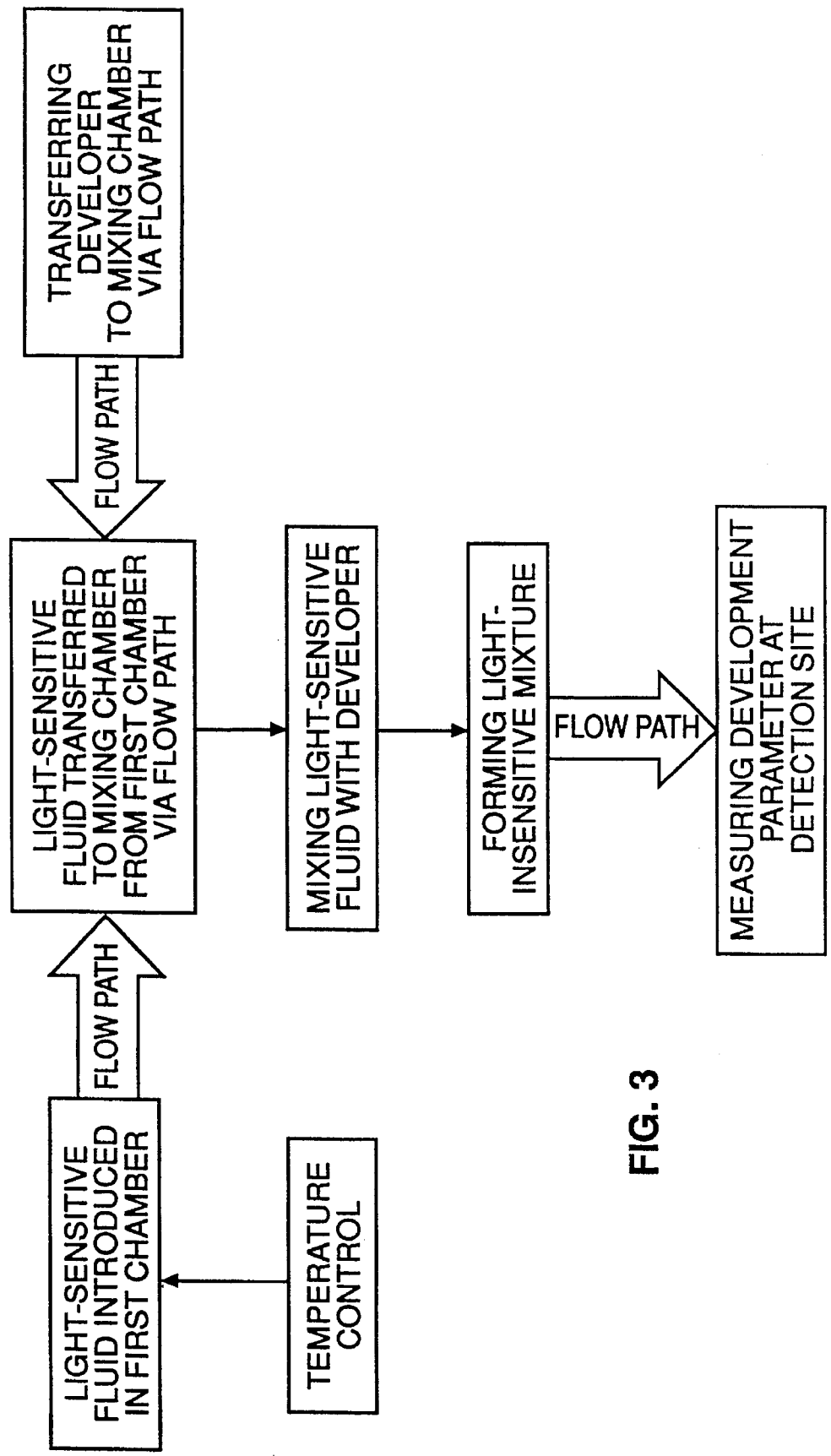
FIG. 3 is a schematic representation of the method of the present invention.

DETAILED DESCRIPTION OF THE PREFERRED EMBODIMENT.

The invention as hereinafter described in connection with the preferred embodiment is useful in measuring the quality of photographic emulsions by the detection of silver particles contained in the reaction product of the developer, emulsion and fixer. In the preferred embodiment five chambers are provided along with channels connecting the chambers, burst seals to seal the chambers, entry ports to fill the chambers, and an exit port through which the photographic emulsion mixture is expelled into an attached vial for measurement of silver particles contained therein using an infrared device. However, the device is not limited to the measurement of a photographic emulsion for fogging, and is also not limited by the number of chambers used, since by the spirit of the invention, modification thereof may be made to adapt the device for other uses, such as, for reacting pharmaceutical chemicals/substances and measuring the quality or quantity of the reacted substances.

Referring to FIGS. 1 through 3, the reference character 10 indicates the pouch-like device of the present invention. The device comprises two superimposed layers of suitable length and width made from flexible or pliable materials such as: polymeric materials including polyethylene, polypropylene, and preferably thermoplastic materials; and metals such as aluminum foil which can be coated with a thermoplastic material. The superimposed layers are joined together along marginal areas 12, 14, 16 and 18 or both at marginal areas 12, 14, 16 and 18 and inwardly extending areas 12', 14' 16' and 18' by heat sealing or adhesively uniting the same, thereby providing a longitudinally extending series of five compartments or chambers to accommodate the reagents and the emulsion to be tested. When the superimposed layers are joined together as above-indicated, a flat pouch is formed providing the device of the present invention, which comprises:

a first chamber 20 pre-filled with a measured amount of a developer;

a second chamber 30 to receive a measured amount of an emulsion just prior to the testing of said emulsion;

a third chamber 40 to receive the developer and emulsion from said first and second chambers;

a fourth chamber 50 parallelly positioned with the third chamber, pre-filled with a measured amount of a fixer; and a fifth chamber 60 to serve as the final reaction chamber.

The fifth chamber is provided with exit port 70 having connecting means, such as snap-on or screw-on means to receive a vial into which the emulsion mixture is expelled for measurement of silver particles contained therein.

Intercommunication between the chambers is provided by conduits or channels so that the content of one chamber may be transferred into another successive chamber. Accordingly: first chamber 20 is connected to second chamber 30 by channel 21; second chamber 30 is connected to third chamber 40 by channel 34; third chamber 40 is connected to fifth chamber 60 by channel 44; and fourth chamber 50 is connected to fifth chamber 60 by channel 51.

First chamber 20 is provided with entry port 28 connected to first chamber 20 via channel 27 through which a measured amount of the developer is introduced into the chamber.

Second chamber 30 is also provided with an entry port 29 connected to second chamber 30 via channel 23 through which a measured amount of the emulsion is introduced into the chamber just prior to testing. Fourth chamber 50 is also provided with an entry port 58 connected to fourth chamber 50 via channel 53 through which a measured amount of the fixer is introduced into the chamber. First and fourth chambers are pre-filled with the developer and fixer respectively.

In another embodiment of the present invention first chamber 20 is equipped with channel 27 without an entry port. Similarly, fourth chamber 50 is equipped with channel 53 without an entry port. Since these chambers are designed to be pre-filled, the channels can be heat sealed after the filling process is completed.

Adjoining chambers of the device are initially closed against intercommunication by burstable separating or sealing means of such character as to open under external pressure applied thereto. The burstable separating or sealing means may comprise narrow transverse heat sealed or adhesive jointure of the relatively small area defined by the entry/exit area of the conduits or channels which readily yield to applied pressure whereby to open communication between the chambers through the channels connecting the chambers. Accordingly: burstable sealing means 23 closes first chamber 20; burstable sealing means 32 closes second chamber 30; burstable sealing means 42 closes third chamber 40; burstable sealing means 52 closes fourth chamber 50; and burstable sealing means 62 closes fifth chamber 60.

As earlier indicated, first chamber 20 is pre-filled with a measured amount of a developer, and fourth chamber 50 is pre-filled with a measured amount of a fixer and the chambers are sealed. When testing of an emulsion is desired, a measured amount of the emulsion is introduced into second chamber 20. The device is then ready to be subjected to the reaction and testing procedure which comprise the following steps.

First chamber 20 is subjected to external pressure by advancing first chamber 20 through a squeeze roller (not shown). The squeeze roller, traveling in a track, is pressing against the pouches which are placed between guide rails to maintain their position. The squeeze roller is equipped with a heated platen the temperature of which can be controlled. The squeeze roller and heated platen are preferably enclosed in a box in which the air surrounding the roller and heated platen can also be heated and its temperature controlled within the desired range of temperatures. As the chamber is squeezed in direction from its outer or receiving end toward its inner end, its developer content is forced toward the burstable sealing means thereby exerting internal pressure against the burstable sealing means which opens the chamber to passage of the developer into the second chamber 30 which contains the emulsion. The developer and emulsion are thereby mixed allowing a reaction to occur. After an interval permitting reaction between the developer and emulsion elapses, second chamber 30 is in turn subjected to squeezing pressure of the squeeze rollers to advance its reacted mixture into third chamber 40. Upon completing the transfer of the reaction mixture, third chamber 40 and fourth chamber 50 being positioned parallel to each other, are simultaneously subjected to pressure exerted thereon by the squeeze rollers so that the contents of the chambers 40 and 50 are simultaneously transferred into chamber 60, wherein an intimate mixing of the contents take place resulting in the reaction of said contents. The resultant content of fifth chamber 60 can, by similar application of squeezing pressure, passed into a glass vial (not shown) through exit port 70. The vial is then ready for test reading and conclusion in any suitable manner, such as reading by an IR photometer, and the fogging or the concentration of silver particles calculated by methods known in the art.

For testing photographic emulsions, first chamber 20 is pre-filled with a developer and fourth chamber 50 is pre-filled with the fixer. The emulsion to be tested is introduced into second chamber 30 just prior to the testing procedure. The temperature of the device is maintained at about 100° F. or higher by controlling the temperature of the box. A dwell time is allowed after mixing the emulsion and the developer and before proceeding with the addition of the fixer. The cycle of the process according to the invention comprises:

placing the device on the platen of the squeeze roller;

starting the roller to mix the emulsion with the developer;

adding the fixer; and expelling the mixture into the vial for reading.

A preferred process of practicing the present invention follows. First chamber 20 is pre-filled with from about 1 to about 2 ml of the developer and fourth chamber 50 is pre-filled with from about 1 to about 2 ml of the fixer. The emulsion to be tested is introduced into second chamber 30 just prior to the testing procedure. A volume of from about 0.1 to about 0.2 ml of the emulsion is introduced thereby maintaining a volume ratio of about 10:1 of the developer/fixer to emulsion. The temperature of the device is to be maintained at about 103° F.–104° F. by controlling the air temperature in the environment and the platen temperature of the squeeze roller. It is also important to allow dwell time during the testing procedure. After mixing the emulsion and developer it is preferred to allow 30 +½ seconds before proceeding with the addition of the fixer. The cycle time for a complete test is about a total of two minutes during which the activities consist of: placing the device on the platen of the squeeze roller and allowing about one minute for the device to reach a temperature of about 103° F.–104° F.; starting the roller to mix the emulsion with the developer; allowing about 30 seconds before adding the fixer and forcing the solution mixture into the vial for reading.

As illustrated by FIG. 3, although five chambers are preferred, fewer chambers can be provided to practice the invention. For example, the developer can be contained in a mixing chamber, thereby reducing the number of chambers. That is, a single chamber can be comprised of (i) the chamber containing the developer and (ii) the mixing chamber.

Filling of the device with the emulsion is accomplished through the entry port using a pipette or other convenient means. Pre-filling the device with the developer and fixer is accomplished through the ports.

It will be obvious to those skilled in the art that various changes and further modifications may be made in the device without departing from the invention as defined by the claims.

What is claimed is:

1. A method of measuring a development parameter of a light-sensitive fluid in a white-light environment comprising:

introducing a predetermined amount of the light-sensitive fluid into a first chamber of a light-impervious containment apparatus;

heating the light-sensitive fluid to a temperature above 100° F.;

applying a predetermined pressure along a flow path between said first chamber and a mixing chamber of said containment apparatus;

bursting a seal positioned across said flow path between said first chamber and said mixing chamber;

transferring the light-sensitive fluid from said first chamber to said mixing chamber;

mixing the light-sensitive fluid with a sufficient amount of developer in said mixing chamber to develop the light-sensitive fluid to a light-insensitive mixture; transferring the light-insensitive mixture to a detection site in communication with said mixing chamber and disposed in the white-light environment; and measuring said development parameter in the white-light environment.

2. The method according to claim 1 further comprising the step of heating the pouch to between about 103° F. and about 104° F.

3. A method for measuring the development of a photographic emulsion having silver particles therein in a white-light environment using a pouch, the pouch having first, second, third, fourth and fifth contiguous chambers sealed by burstable seals and connected by channels, the method comprising the steps of:

(a) pre-filling the first chamber with a measured amount of a developer;

(b) pre-filling the fourth chamber with a measured amount of a fixer;

(c) adding a measured amount of the emulsion to be tested to the second chamber;

(d) heating the pouch to a temperature above about 100° F.;

(e) bursting the developer seal and transferring the developer by external pressure means into the second chamber;

(f) flowing the content of the second chamber into the third chamber by exerting an external pressure onto the second chamber and allowing the mixture a dwell time of about 30 seconds to allow for the reaction of the developer and the emulsion;

(g) exerting an external pressure simultaneously on the third and fourth chambers thereby transferring their contents into the fifth chamber and allowing them to mix to obtain a final, reacted emulsion;

(h) transferring the reacted emulsion into a detachable vial attached to the fifth chamber by exerting an external pressure onto the fifth chamber; and (i) taking a photometric reading of the filled vial using an infrared device to determine the amount of silver particles in the reacted emulsion.

* * * * *